United States Patent [19]

Degenhardt et al.

[11] Patent Number: 5,009,882
[45] Date of Patent: Apr. 23, 1991

[54] USE OF A CARBOXY STARCH POLYMER TO INHIBIT PLAQUE WITHOUT TOOTH STAINING

[75] Inventors: Charles R. Degenhardt; Barbara A. Kozikowski, both of Cincinnati, Ohio

[73] Assignee: The Proctor & Gamble Company, Cincinnati, Ohio

[21] Appl. No.: 526,930

[22] Filed: May 21, 1990

[51] Int. Cl.$^5$ .................. A61K 7/16; A61K 7/18; A61K 9/68
[52] U.S. Cl. .................. 424/52; 424/48; 514/778
[58] Field of Search .............. 424/48, 49, 52; 514/778

[56] References Cited

U.S. PATENT DOCUMENTS

| | | | |
|---|---|---|---|
| 3,665,000 | 5/1972 | Hills et al. | 260/233.3 |
| 3,679,795 | 7/1972 | De Somer et al. | 424/180 |
| 3,719,514 | 3/1973 | Taylor | 106/210 |
| 3,784,475 | 1/1974 | Diehl | 252/89 |
| 4,004,039 | 1/1977 | Shoaf et al. | 426/548 |
| 4,673,704 | 6/1987 | Flesher et al. | 524/519 |
| 4,778,836 | 10/1988 | Farrar et al. | 524/35 |

Primary Examiner—Shep K. Rose
Attorney, Agent, or Firm—L. W. Lewis; J. J. Yetter; R. C. Witte

[57] ABSTRACT

The present invention relates to compositions and methods for inhibiting plaque. In particular, this invention relates to oral compositions comprising: (a) a safe and effective amount of a plaque-inhibiting carboxy starch polymer comprising the formula

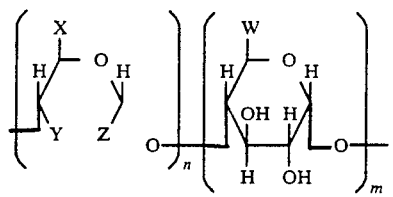

wherein W and X are independently selected from $CH_2OH$, CHO and $CO_2H$, or the neutralized carboxylic acid salts thereof, Y and Z are independently selected from CHO and $CO_2H$, or the neutralized carboxylic acid salts thereof, n is in the range of from about 5 to about 2500, m is in the range of from 0 to about 2500, provided that the sum of n and m ranges from about 5 to about 2500, and the degree of carboxylation of said active agent ranges from about 1 to about 3; and (b) a pharmaceutically acceptable carrier. These compositions inhibit plaque without staining the teeth which are contacted with the composition.

This invention also relates to a method of inhibiting plaque on tooth surfaces in the oral cavity. This method involves applying a safe and effective amount of the carboxy starch polymer active agent to the oral cavity. Such an application is typically made by applying the above-described oral compositions containing the carboxy starch polymer to the oral cavity. The application does not stain the teeth on which it is made.

26 Claims, No Drawings

USE OF A CARBOXY STARCH POLYMER TO INHIBIT PLAQUE WITHOUT TOOTH STAINING

TECHNICAL FIELD

The present invention relates to a method of inhibiting plaque formation on teeth. In particular, it relates to a method of inhibiting plaque formation on teeth wherein the tooth surface is coated with a carboxy starch polymer active agent. This invention also relates to oral compositions containing said active agent and a pharmaceutically acceptable carrier.

BACKGROUND OF THE INVENTION

Dental plaque is a combination of minerals and bacteria. The bacteria associated with plaque can cause inflammatory gingivitis. Gingivitis, in turn, may lead to periodontitis. Therefore, it would be highly desirable to develop compositions and methods for inhibiting plaque. As such, numerous compositions and methods for inhibiting the formation of plaque are reported in the literature.

U.S. Pat. No. 4,847,070, issued July 11, 1989, to Pyrz et al., discloses oral compositions which are effective against calculus and contain a chelating agent which is an acrylic acid polymer or copolymer or EDTA, a strontium ion source, a fluoride ion source, a pyrophosphate ion source, and a pharmaceutically acceptable carrier. The mass average molecular weight of the acrylic acid polymer or copolymer used in this invention may be in the range of about 1,000 to about 1,200,000.

U.S. Pat No. 4,816,245, issued Mar. 28, 1989, to Gaffar, discloses a method of inhibiting human dental plaque and gingivitis involving regular application to the oral cavity of an oral composition containing an effective plaque- and gingivitis-inhibiting amount of polyvinyl phosphonic acid, or salt thereof, having a number average molecular weight of about 4,000 to 9,100.

U.S. Pat. No. 4,775,525, issued Oct. 4, 1988, to Pera, discloses a dental treatment composition and method for reducing dental plaque. The disclosed method comprises treating dental surfaces with a composition containing sodium alginate, which acts as a calcium ion chelating agent which weakens the bond between the plaque and the teeth, thereby allowing easy removal of the plaque by subsequent brushing. The compositions disclosed in this patent may also contain benzalkonium chloride and zinc sulfate, which provide for desensitizing the teeth and eliminating of halitosis.

U.S. Pat. No. 4,759,925, issued July 26, 1988, to Gaffar et al., discloses the use of a mixture of the perfluoroalkyl surfactant of the general formula $C_xF_{2x+1}(CH_2)_nS(CH_2)n'CO_2M$, wherein x is an integer of 3–8, n and n' are independently integers of 2 to 4, and M is hydrogen, and an alkali metal or ammonium as a dentifrice or a mouthwash with the benefit of preventing plaque formation.

U.S. Pat. No. 4,627,977, issued Dec. 9, 1986, to Gaffar et al., discloses an oral composition containing a calculus inhibiting amount of a linear molecularly dehydrated polyphosphate salt and, to inhibit enzymatic hydrolysis of said polyphosphate salt in saliva, a combination of a fluoride ion-providing source and a synthetic anionic linear polymeric polycarboxylate.

U.S. Pat. No. 4,528,179, issued July 9, 1985, to Gaffar, discloses a method of inhibiting human dental plaque and gingivitis by the regular application to the oral cavity of an oral composition containing an effective plaque- and gingivitis inhibiting amount of polyvinyl phosphonic acid or salt thereof. The polyvinyl phosphonic acid of this reference has a preferred number average molecular weight of about 6,000 to about 100,000.

U.S. Pat. No. 4,428,930, issued Jan. 31, 1984, to Chang, discloses a dentifrice composition containing a water-dispersible, membrane-forming material which, when applied to tooth surfaces in an oral environment, attaches thereto and forms a substantially continuous hydrophobic barrier thereon, which hydrophobic barrier substantially reduces elution of a previously applied therapeutic agent. This patent also discloses a method for inhibiting plaque formation on teeth which comprises contacting the teeth with an effective amount of the above-described composition. Polymeric anionic membrane forming materials disclosed as useful in the compositions of this patent include a class of polymers having a polyolefinic main chain with acid functionalities pendent therefrom. Typical of the materials which can comprise the polyolefinic main chain are polymers of ethylene, propylene, styrene, unsaturated carboxylic acids, and copolymers of two or more of these materials. Representative polymeric anionic membrane forming materials disclosed as useful in the compositions of this patent include polyacrylic acid having a molecular weight in the range of 2,000 to 4,000,000; sodium polystyrenesulfonate having a molecular weight in the range of about 5,000 to 6,000,000; "Gantrez AN", available from GAF corporation; polyvinyl phosphate; and copolymers of acrylates which contain pendent carboxyl groups.

U.S. Pat. No. 4,375,461, issued Mar. 1, 1983, to Gander et al., discloses compositions and methods for preventing the attachment of dental plaque to the surfaces of the teeth of mammals. These disclosed compositions and methods comprise certain sulfonated vinylaromatic homopolymers and copolymers and the pharmaceutically acceptable salts thereof in a pharmaceutically acceptable vehicle, and a periodic application thereof to teeth. Hydrophilic polymeric anionic sulfates useful for dental plaque control in accordance with the disclosure of this patent are essentially sulfonated homopolymers of both unsubstituted and substituted stryene, 1-vinylnaphthalene, 2-vinylnaphthalene, and acenaphthylene, and certain copolymers thereof. Representative examples of vinyl aromatic monomers, homopolymers, and copolymers which are available in commerce and can be converted to the hydrophilic polymeric sulfonates of this patent are the following: (a) polystyrene and sodium polystyrene sulfonate of varying molecular weights available from Pressure Chemical Company; (b) styrene/butadiene (85/15) copolymer; (c) styrene/isobutylene (60/40) copolymer; (d) vinylbenzyl chloride monomer, 60/40 meta-/paraisomers, available from Dow Chemical Company; and (e) halostyrene monomers available from Polysciences Inc., and Aldrich Chemical Company.

U.S. Pat. No. 4,362,713, issued Dec. 7, 1982, to Buck, discloses compositions and methods for preventing the attachment of dental plaque to the teeth of mammals. The disclosed compositions and methods comprise certain salts of certain maleic acid copolymers in a pharmaceutically acceptable vehicle and the periodic application thereof to teeth. This patent further discloses that certain hydrophilic alkali metal and ammonium salts of 1:1 copolymers of styrene and maleic acid and 1:1 copolymers of certain linear 1-alkenes and maleic acid have been found to inhibit the deposition of dental plaque onto human teeth when applied thereon.

U.S. Pat. No. 4,224,309, issued Sept. 23, 1980, to Gaffar et al., discloses an oral composition containing an antibacterial antiplaque agent and an anti-stain additive which reduces staining caused by the antibacterial antiplaque agent, without substantially diminishing the activity of the antibacterial antiplaque agent. Bis-biguanido hexanes, such as chlorhexidine and alexidene, and quaternary ammonium salts, such as benzethonium chloride and cetyl pyridinum chloride, are typical examples of antibacterial agents. The anti-stain additive is 2-phosphono-butane-1,2,4-tricarboxylic acid or an orally acceptable salt thereof.

U.S. Pat. No. 4,138,477, issued Feb. 6, 1979, to Gaffar, discloses a composition which is useful for the prevention and control of mouth odor and is also effective in preventing calculus, plaque, caries and periodontal disease. This composition contains, as its essential agent, a zinc-polymer combination formed by the reaction or interaction of a zinc compound with an anionic polymer containing carboxylic, sulfonic and/or phosphonic acid radicals.

U.S. Pat. No. 4,118,474, issued Oct. 3, 1978, to Gaffar et al., discloses an antibacterial oral composition effective to promote oral hygiene which contains an antibacterial antiplaque agent and an additive for reducing staining of dental surfaces without substantially diminishing the activity of the antibacterial and antiplaque agent. Bis-biguanido hexanes, such as chlorhexidine and alexidine, and quaternary ammonium salts, such as benzethonium chloride and cetyl pyridinium chloride, are typical examples of antibacterial antiplaque agents. The antistain additive is phosphonoacetic acid or salts thereof.

U.S. Pat. No. 4,118,473, issued Oct. 3, 1978, to Gaffar et al., discloses an antibacterial oral composition effective to promote oral hygiene which contains an antibacterial antiplaque agent and an additive for reducing staining of dental surfaces without substantially diminishing the activity of the antibacterial and antiplaque agent. Bis-biguanido hexanes, such as chlorhexidine and alexidine, and quaternary ammonium salts, such as benzethonium chloride and cetyl pyridinum chloride, are typical examples of antibacterial antiplaque agents. The antistain additive is an N-methylene phosphonate compound, such as iminodiacetic N-methylene phosphonic acid and salts thereof.

United Kingdom Patent Application 2151478-A, published July 24, 1985, assigned to the Colgate-Palmolive Company, discloses that dental plaque and gingivitis are inhibited by the regular application to the oral cavity of an oral composition containing an effective plaque- and gingivitis-inhibiting amount of polyvinyl phosphonic acid or a salt thereof. The polyvinyl phosphonic acid, and salt thereof, have a preferred number average molecular weight of from about 6,000 to 100,000.

In spite of the many disclosures of agents for inhibiting and reducing plaque, the need for improved antiplaque products still exists, particularly for antiplaque products that do not cause staining of the teeth.

It is therefore an object of the present invention to provide a method for inhibiting plaque formation on teeth, without tooth staining, by applying a plaque-inhibiting carboxy starch polymer active agent to the oral cavity.

It is another object of the present invention to provide for compositions containing such carboxy starch polymer and a pharmaceutically acceptable carrier.

These objects will be realized by the present invention.

SUMMARY OF THE INVENTION

The present invention embraces oral compositions comprising: (a) a safe and effective amount of a plaque-inhibiting carboxy starch polymer comprising the formula

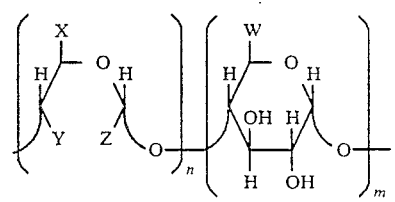

wherein W and X are independently selected from $CH_2OH$, $CHO$ and $CO_2H$, or the neutralized carboxylic acid salts thereof, Y and Z are independently selected from $CHO$ and $CO_2H$, or the neutralized carboxylic acid salts thereof, n is in the range of from about 5 to about 2500, m is in the range of from 0 to about 2500, provided that the sum of n and m ranges from about 5 to about 2500, and the degree of carboxylation of said polymer ranges from about 1 to about 3; and (b) a pharmaceutically acceptable carrier.

The present invention also encompasses a method for inhibiting plaque formation on the teeth.

DETAILED DESCRIPTION OF THE INVENTION

The oral compositions of the present invention are useful for inhibiting plaque and comprise: (a) a safe and effective amount of a plaque-inhibiting carboxy starch polymer and (b) a pharmaceutically acceptable carrier. The compositions of this invention may optionally contain additional ingredients which include, but are not limited to, a fluoride ion source, flavoring agents, sweetening agents, and emulsifying agents.

"Oral compositions", as used herein, means a product which in the ordinary course of usage is retained in the oral cavity for a time sufficient to contact substantially all the dental surfaces and/or oral tissues.

"Safe and effective amount", as used herein for the oral compositions of the present invention, means a sufficient amount of material contained in such compositions for inhibiting the formation of plaque in the oral cavity while being safe to the hard and soft tissues of the oral cavity.

The term "comprising", as used herein, means that various additional components can be employed in the compositions of this invention, as long as the listed materials can perform their intended functions.

The term "pharmaceutically acceptable carrier", as used herein, means a suitable vehicle which is pharmaceutically acceptable for application inside the oral cavity and can be used to apply the present compositions in the oral cavity.

Carboxy Starch Polymer Active Agent

The carboxy starch polymer useful as the plaque-inhibiting active agent in the compositions of the present invention is of the formula:

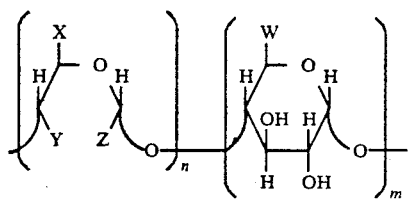

(I)

wherein W and X are independently selected from $CH_2OH$, CHO and $CO_2H$, preferably from $CH_2OH$ and $CO_2H$, or the neutralized carboxylic acid salts thereof, Y and Z are independently selected from CHO and $CO_2H$, or the neutralized carboxylic acid salts thereof, n is in the range of from about 5 to about 2500, preferably from about 5 to about 1500, most preferably from about 5 to about 1000, m is in the range of from 0 to about 2500, preferably from 0 to about 1500, most preferably from 0 to about 1000, provided that the sum of n and m ranges from about 5 to about 2500, preferably from about 5 to about 1500, most preferably from about 5 to about 1000. The degree of carboxylation of the carboxy starch polymer typically ranges from about 1 to about 3, preferably from about 1.5 to about 3, most preferably from about 1.7 to about 3. The phrase "degree of carboxylation" is defined as the number average of carboxy groups per starch monomer contained in the polymer chain. The term "monomer" refers to the individual starch groups having either the n or m subscript, and not the two-monomer structure shown as compound I. The mass average molecular weight of the carboxy starch polymer typically ranges from about 1,000 to about 500,000, preferably from about 1,000 to about 300,000.

The polymer of the present invention may comprise repeating units of the two-monomer block shown as structure I, it may comprise a block copolymer, such as when a long chain of the monomer having the n subscript is joined with a long chain of the monomer having the m subscript, it may comprise a random mixture of the individual monomers of the two-monomer block shown as structure I, or it may comprise solely the monomer having the n subscript, as when m is zero, of the two-monomer block shown as structure I.

The carboxy starches of the present invention are typically prepared by the oxidation of a dialdehyde starch. The dialdehyde starch may be obtained through the procedure disclosed in "Methods in Carbohydrate Chemistry" Volume IV, page 316, the disclosure of which is incorporated herein by reference. In this procedure, a solution containing sodium metaperiodate and water is added to a stirred suspension containing starch and water. The resulting mixture is stirred at room temperature for a period of time, and the solid dialdehyde starch product is isolated by filtration and dried.

The dialdehyde starch is typically converted to the desired carboxy starch polymer by oxidation with either chlorous acid, as shown in U.S. Pat. No. 3,784,475, issued Jan. 8, 1974, to Diehl, the disclosure of which is incorporated herein by reference, or with dinitrogen tetroxide, as shown in U.S. Pat. No. 3,665,000, issued May 23, 1972, to Hills, the disclosure of which is incorporated herein by reference.

In a typical chlorous acid oxidation, dialdehyde starch is added to an aqueous solution containing sodium chlorite and acetic acid. The mixture is stirred at room temperature for a period of time. Air is then bubbled through the mixture until a clear solution is obtained and the pH is adjusted using a sodium hydroxide solution. The reaction mixture is then poured onto ethanol to precipitate the product, which is isolated by filtration and dried.

In a typical dinitrogen tetroxide oxidation, a reaction vessel is charged with a solution of dinitrogen tetroxide in methylene chloride at low temperatures. The solution is stirred vigorously as dialdehyde starch is added, and the mixture is allowed to warm to room temperature with stirring. After a period of time, additional dinitrogen tetroxide is added, and stirring is continued. Argon gas is bubbled through the reaction mixture to remove nitrous oxide. The white solid product is then filtered, washed with water, and dried.

Preferred starch polymers useful in the present invention are of the general formulas:

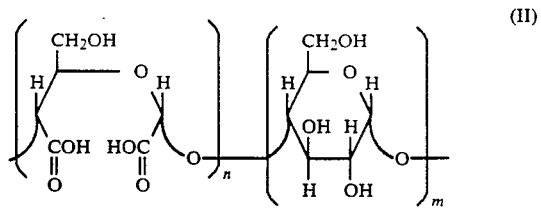

(II)

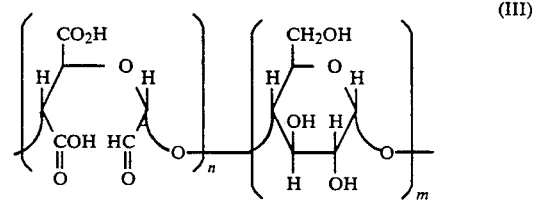

(III)

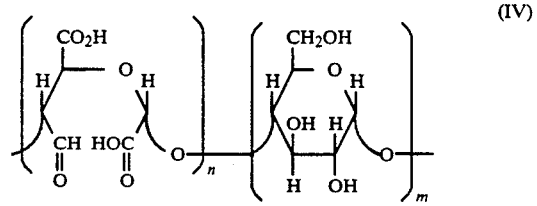

(IV)

or the neutralized carboxylic acid salts thereof, wherein n and m are as hereinbefore defined. The number average degree of carboxylation of these preferred starch polymers typically is in the range of from about 1 to about 2.5, more typically from about 1.5 to about 2, most typically from about 1.5 to about 1.9. The mass average molecular weight of these preferred starch polymers is typically in the range of from about 1,000 to about 500,000, preferably from about 4,000 to about 250,000, most preferably from about 50,000 to about 250,000.

These preferred starch polymers may be prepared by the methods disclosed in "Chlorous Acid Oxidation of Periodate Oxidized Cornstarch", B. T. Hofreiter, I.A. Wolff and C. L. Mehltretter, *J. Amer. Chem Soc.*, 79, 6457 (1957), the disclosure of which is incorporated herein by reference.

Individually, these preferred carboxy starch polymers may comprise repeating units of the two-monomer blocks shown as structures II, III and IV, they may comprise a block copolymer, such as when a long chain of the monomer having the n subscript is joined with a long chain of the monomer having the m subscript, they may comprise a random mixture of the individual monomers of the two-monomer blocks shown as structures II, III and IV, or they may comprise solely the monomer having the n subscript, as when m is zero, of the two-monomer blocks shown as structures II, III and IV.

The carboxy starch polymer composition of the present invention may be comprised of random mixtures of the two-monomer blocks shown as structures II–IV. Additionally, the individual monomers containing the m and n subscripts in structures II-IV may be randomly distributed throughout the polymer chain length of the carboxy starch polymers of the present invention.

When the polymer of the present invention is prepared by the methods hereinbefore referenced, and is comprised of a mixture of structures II-IV, such polymer will typically comprise from about 25% to 100%, more typically from about 50% to about 90%, most typically from about 70% to about 90% of structure II, with the balance being comprised of structures III and IV.

A fourth preferred starch polymer useful in the present invention is of the general formula:

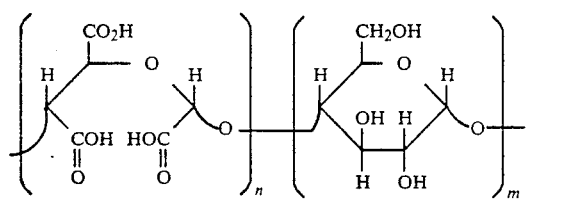

(V)

or the neutralized carboxylic acid salts thereof, wherein n is in the range of from about 5 to about 250, preferably from about 5 to about 150, most preferably from about 5 to about 100, and m is in the range of from 0 to about 250, preferably from 0 to about 150, most preferably from 0 to about 100, provided that the sum of n and m is in the range of from about 5 to about 250, preferably from about 5 to about 150, most preferably from about 5 to about 100. The number average degree of carboxylation of this fourth preferred starch polymer typically ranges from about 1.5 to about 3, preferably from about 2 to about 3, most preferably from about 2.5 to about 3. The mass average molecular weight of this fourth preferred starch polymer typically ranges from about 1,000 to about 50,000, preferably from about 1,000 to about 20,000.

This fourth preferred starch polymer may be prepared as described in U.S. Pat. No. 3,665,000, issued May 23, 1972, to Hills et al., the disclosure of which is incorporated herein by reference.

This fourth preferred starch polymer may comprise repeating units of the two-monomer block shown in structure V, it may comprise a block copolymer, such as when a long chain of the monomer having the n subscript is joined with a long chain of the monomer having the m subscript, it may comprise a random mixture of the individual monomers of the two-monomer block shown in structure V, or it may comprise solely either the monomer having the n subscript, as when m is zero, of the two-monomer block shown in structure V.

Mixtures of the starch polymers of the present invention may be used as the plaque-inhibiting active agent in the compositions of the present invention, including mixtures of the four preferred starch polymers discussed herein. The mass average molecular weight of active agent in such polymer mixture typically ranges from about 1,000 to about 250,000, preferably from about 3,000 to about 200,000, most preferably from about 5,000 to about 100,000. Mixtures of high molecular weight and low molecular weight starch polymer material may be used to achieve a polymer mixture having an appropriate mass average molecular weight. When mixtures of starch polymers are used as the plaque-inhibiting active agent in the compositions of the present invention, the number average degree of carboxylation for the polymer mixture typically ranges from about 1 to about 3, preferably from about 1.5 to about 3, most preferably from about 1.7 to about 2.5.

When the neutralized carboxylic acid salts of the starch polymers useful in the present invention are prepared, one or more of the available carboxylic acid groups on the polymer will be neutralized with alkali metal or quaternary ammonium cations, with alkali metals being preferred, and sodium being most preferred.

The degree of carboxylation of the final carboxy starch product is dependent upon the method of oxidation used, the stoichiometry of the oxidation used, the stoichiometry of the oxidation reaction, and the level of oxidation of the dialdehyde starch starting material. However, achieving the desired degree of carboxylation is well within the ability of one skilled in the art. In general, oxidation using chlorous acid will produce carboxy starch polymers with a degree of carboxylation in the range of from about 1.0 to about 2.0, while dinitrogen tetroxide tends to generate carboxy starches with a degree of carboxylation in the range of from about 1.3 to about 3.0.

The degree of carboxylation in the carboxy starch polymers is determined by potentiometric titration with sodium hydroxide after ion exchange to the free acid form. Carboxy-starches give points in the pH range of 8.0-9 0. relatively sharp inflection Residual alkalinity (assumed to be sodium carbonate) is determined by titration with hydrochloric acid to the phenolphthalein endpoint. Dialdehyde content is determined by a time reaction with sodium hydroxide at 70° C. Moisture is determined by Karl Fischer titration.

The carboxy starch polymer useful in the present invention may optionally be interspersed with non-starch monomers. Preferred are monomers which add additional carboxylate groups to the polymer. Most preferred are acrylic acid and acrylate monomers.

The amount of plaque-inhibiting carboxy starch polymer active agent used in the compositions of the present invention generally ranges from about 0.1% to about 10% by weight, preferably from about 1% to about 8% by weight, most preferably from about 3% to about 5% by weight. For a dentifrice composition, the most preferred concentration of active agent ranges from about 3% to about 5% by weight. For a mouthwash composition, the most preferred concentration of active agent ranges from about 3% to about 5% by weight.

As discussed above, the carboxy starch polymers of the present invention are useful for inhibiting the formation of plaque on the tooth surface. While not intending to necessarily be limited thereby, it is believed that these plaque-inhibiting carboxy starch polymer active agents are additionally beneficial in that they inhibit plaque formation without discernibly staining the surface of the treated teeth.

Pharmaceutically Acceptable Carrier

The carrier for the plaque-inhibiting active agent of the present invention can be any vehicle suitable for use in the oral cavity, including the usual components of mouthwashes, toothpastes, topical dental gels, toothpowders, prophylaxis pastes, lozenges, gums and the like, and are more fully described hereinafter. Dentifrices and mouthwashes are the preferred systems, with toothpastes being the more preferred.

Toothpastes and toothpowders contain as a major component an abrasive. The abrasive polishing material contemplated for use in the present invention can be any material which does not excessively abrade dentin. These include, for example, silicas including gels and precipitates, calcium carbonate, dicalcium orthophosphate dihydrate, calcium pyrophosphate, tricalcium phosphate, calcium polymetaphosphate, insoluble sodium polymetaphosphate, hydrated alumina, and resinous abrasive materials such as particulate condensation products of urea and formaldehyde, and others such as disclosed by Cooley et al., in U.S. Pat. No. 3,070,510, issued Dec. 25, 1962, which is incorporated herein by reference. Mixtures of abrasives may also be used.

Various types of silica dental abrasives can provide the unique benefits of exceptional dental cleaning and polishing performance without unduly abrading tooth enamel or dentin. Silica abrasive materials are also exceptionally compatible with sources of soluble fluoride and other ion sources. For these reasons they are preferred for use herein. Of course the abrasive selected should also exhibit excellent compatibility with soluble strontium ion sources.

The silica abrasive polishing materials useful herein, as well as the other abrasives, generally have an average particle size ranging between about 0.1 and 30 microns, preferably between 5 and 15 microns. The silica abrasive can be precipitated silica or silica gels such as the silica xerogels described in Pader et al., U.S. Pat. No. 3,538,230, issued Mar. 2, 1970 and DiGiulio, U.S. Pat. No. 3,862,307, issued June 21, 1975, both of which are incorporated herein by reference. Preferred are the silica xerogels marketed under the tradename "Syloid" by the W.R. Grace & Company, Davidson Chemical Division. Preferred precipitated silica materials include those marketed by the J. M. Humber Corporation under the tradename "Zeodent", particularly the silica carrying the designation "Zeodent 119. These silica abrasives are described in U.S. Pat. No. 4,340,583, issued July 29, 1982, the disclosure of which is incorporated herein by reference.

The abrasive in the dentifrice compositions described herein is present at a level of from about 6% to about 70%, preferably from about 15% to about 25% when the dentifrice is a toothpaste. Higher levels, as high as 90%, may be used if the composition is a toothpowder.

Another embodiment of the prevent invention is a mouthwash composition. Conventional mouthwash compositions components can comprise the carrier for the actives of the present invention. Mouthwashes generally comprise from about 20:1 to about 2:1 of a water-/ethyl alcohol solution and preferably other ingredients such as flavoring agents, sweeteners, humectants and sudsing agents such as those described above. The humectants, such as glycerin and sorbitol, give a moist feel to the mouth. Generally, on a weight basis the mouthwashes of the invention comprise from about 5% to about 60%, preferably from about 10% to about 25%, of ethyl alcohol; from 0% to about 20%, preferably from about 5% to about 20%, of a humectant; from 0% to about 2%, preferably from about 0.01% to about 0.15%, of an emulsifying agent; from 0% to about 0.5%, preferably from about 0.005% to about 06%, of a sweetening agent such as saccharin; from 0% to about 0.3%, preferably from about 0.03% to about 0.3%, of a flavoring agent; and the balance water.

Suitable lozenge and chewing gum components are disclosed in U.S. Pat. No. 4,083,955, issued Apr. 11, 1978 to Grabenstetter et al., which is incorporated herein by reference.

Suitable topical dental gels generally comprise a base of a humectant such as glycerin thickened with a suitable agent. Such gels generally do not contain an abrasive.

The plaque-inhibiting active agents of the present invention have been shown to be highly effective in reducing the deposition of plaque on the tooth surface in in vitro testing.

The in vitro test procedure employed in ascertaining the plaque-inhibiting properties of said active agents is carried out follows: 25 mgs. of hydroxyapatite (HAP) beads are precoated with human saliva for 1.5 hours. The HAP beads are then washed three times with a buffer solution of 0.05M KCl, 1 mM $PO_4$ (pH 6.0), 1 mM $CaCl_2$ and 0.1 mM $MgCl_2$. The HAP beads are then equilibrated with an aqueous solution of a carboxy starch polymer (at a desired concentration such as 5%), at pH 7.0, for 5 minutes with agitation. The HAP beads are removed from the aqueous solution and then washed once with a buffer solution as described above.

For the bacteria adsorption studies 25 mg of the HAP beads prepared as described above are placed in 1.0 ml of a cell suspension comprising about $1.5 \times 10^8$ $^3$H radiolabelled bacteria (*S. sanguis*) in a buffer solution as described above. The beads are equilibrated in the mixture for three hours, with agitation. The beads are allowed to settle for one minute and the supernatant, which contains unadsorbed cells, is removed. The HAP beads are washed three times with buffer solution (same composition as described above), collected by filtration, and dissolved in hydrochloric acid. Radioactivity of the dissolved HAP is then measured by liquid scintillation counts in order to determine the number of bound cells. These results are compared to the radioactivity of dissolved HAP that was prepared as a control without antiplaque agents.

OPTIONAL INGREDIENTS FOR USE IN ORAL COMPOSITIONS

In addition to the above-described components, the oral compositions of the present invention may include a number of optional ingredients.

Such optional ingredients include a safe and effective amount of a fluoride ion source, which typically is in the form of a water-soluble fluoride compound. This water-soluble fluoride compound is typically present in the compositions of this invention in an amount sufficient to give a fluoride concentration of from about 0.0025% to about 5.0% by weight, preferably from about 0.005% to about 2.0% by weight. Preferred fluorides are sodium fluoride, stannous fluoride, indium fluoride, acidulated phosphate fluoride and sodium monofluorophosphate. U.S. Pat. No. 2,946,735, issued July 26, 1960 to Norris et al., and U.S. Pat. No. 3,678,154, issued July 18, 1972 to Widder et al., disclose such salts as well as others. The disclosures of these patents are incorporated herein by reference.

Flavoring agents can also be added to the dentifrice and other compositions of the present invention. Suitable flavoring agents include oil of wintergreen, oil of peppermint, oil of spearmint, oil of sassafras and oil of clove. Sweetening agents are also useful and include aspartame, acesulfame, saccharin, dextrose, levulose and sodium cyclamate. Flavoring and sweetening agents are generally used in the compositions herein at levels of from about 0.005% to about 2% by weight.

The compositions of this invention may also contain emulsifying agents. Suitable emulsifying agents are those which are reasonably stable and foam throughout a wide pH range, and include non-soap anionic, nonionic, cationic, zwitterionic and amphoteric organic synthetic detergents. Many of these suitable surfactants are disclosed by Gieske et al. in U.S. Pat. No. 4,051,234, issued Sept. 27, 1977, which is incorporated herein by reference.

Water may also be present in the compositions of this invention. Water employed in the preparation of commercially suitable compositions should preferably be deionized and free of organic impurities. Water generally comprises from about 10% to about 50% by weight, preferably from about 20% to about 40% by weight, of the toothpaste compositions herein. These amounts of water include the free water which is added plus that which is introduced with other materials, such as with sorbitol.

In preparing toothpastes, it is necessary to add some thickening material to provide a desirable consistency. Preferred thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as gum karaya, gum arabic and gum tragacanth, and polysaccharide gums such as xanthan gum can also be used. Colloidal magnesium aluminum silicate or finely divided silica can be used as part of the thickening agent to further improve texture. Thickening agents in an amount from about 0.5% to about 5.0% by weight of the total composition may be used.

It is also desirable to include a humectant in a toothpaste to keep it from hardening. Suitable humectants include glycerin, sorbitol and other edible polyhydric alcohols at a level of from about 10% to about 70% by weight.

The pH of the present compositions and/or its pH in the mouth can be any pH which is safe for the mouth's hard and soft tissues. Such pH's are generally from about 3 to about 10, preferably from about 4 to about 9.

In addition to the above-described oral compositions, the present invention also encompasses a method of inhibiting plaque on treated tooth surfaces. This method involves applying a safe and effective amount of the carboxy starch polymer of the present invention, in unit dosage form, to the tooth surface. The term "safe and effective amount," as used herein for the method of inhibiting plaque, means a sufficient amount in unit dosage form, typically about 0.125 grams, preferably about 0.100 grams, most preferably about 0.075 grams, of carboxy starch polymer applied to the oral cavity for inhibiting the formation of plaque in the oral cavity, while being safe to the hard and soft tissues of the oral cavity. Such an application is typically made by applying the above-described oral compositions to the oral cavity. When the oral composition is a toothpaste, typically 1.5 grams of toothpaste containing 5 wt. % of the carboxy starch polymer of the present invention is applied to an applicating device, e.g., a toothbrush. The applicating device is then contacted with the tooth surface in a manner such that the oral composition is contacted with the tooth surface. The applicating device may be further used to effect an even distribution of the oral composition onto said tooth surface, for example by brushing. The brushing will preferably last for a period of 2 minutes, although the actual time period of brushing is dependent upon the individual user. Following brushing, the toothpaste residue is typically removed from the tooth surface by using a liquid acceptable to the oral cavity, typically water, to rinse the oral cavity. Typically 10 ml. of water will suffice for such rinsing.

When the oral composition is embodied in a mouthwash, typically 10 ml. of liquid mouthwash containing 5 wt. % of the carboxy starch polymer of the present invention is introduced to the oral cavity. The liquid mouthwash is then agitated, preferably for a period of 2 minutes, within the oral cavity to obtain an improved distribution of the mouthwash over the tooth surface. The actual time of agitation is dependent upon the individual user. Following agitation, the mouthwash is typically expectorated from the oral cavity.

EXAMPLES

The following are representative oral compositions of the present invention.

EXAMPLE I

This example shows the synthesis of a carboxy starch polymer. The following steps are performed:

A solution containing 90.45 g of $NaClO_2$ in 1 l. $H_2O$ is initially prepared. 28.6 ml of acetic acid and 20.0 g of dialdehyde starch are added, in order, to this initial solution, and the resulting reaction mixture is stirred for 22 hrs. at room temperature. The reaction mixture is then aerated with argon and the pH is adjusted to 8-9 using 50% NaOH solution. The mixture is poured into 1 l. of ethanol, and a solid crude reaction product is isolated by decantation. The reaction product is then dissolved in 200 ml of $H_2O$ to form a second solution. This second solution is poured into 600 ml ethanol, and the solid product is again isolated by filtration, dissolved in $H_2O$, and is then lyophilized to produce 6.33 g of white solid carboxy starch. The degree of carboxylation of the white solid carboxy starch is determined to be approximately 1.7 by potentiometric titration.

EXAMPLE II

The following is a representative example of a toothpaste of the present invention.

| Component | Wt % |
| --- | --- |
| Distilled Water | 17.50 |
| Sorbitol (70% Aqueous Solution) | 49.56 |
| Sodium Saccharin | 0.30 |
| Dye Solution | 0.35 |
| Precipitated Silica | 20.00 |
| Sodium Fluoride | 0.25 |
| Flavor | 1.30 |

| Component | Wt % |
|---|---|
| Sodium Alkyl Sulfate (27.9% Aqueous Solution) | 5.00 |
| Carbopol 940S (Available from B. F. Goodrich) | 0.20 |
| Xanthan Gum | 0.60 |
| Carboxy Starch Polymer of Example I | 5.00 |
| | 100.00 |

The above composition is made by combining the water and part of the sorbitol in an agitated mixture and heating this mixture to 140° F. The carboxy starch polymer, saccharin, sodium fluoride and precipitated silica are then added in order and the total mixture is mixed for from 5 to 10 minutes. The flavor, dye and surfactant are then added. In a separate vessel the remainder of the sorbitol, the Carbopol and the xanthan gum are slurried together and then added to the main mix tank. The complete batch is mixed for about one-half hour and subsequently milled and deaerated.

EXAMPLE III

This example illustrates the preparation of a typical carboxy starch polymer of this invention.

A reaction vessel is charged with 8.0 parts of corn starch and 400 parts of water at 80° C. The resulting suspension is cooled to 0° to 5° C., whereupon 16.1 parts of sodium metaperiodate are added. The pH of the mixture is adjusted to a level of 5.0 by the addition of sufficient glacial acetic acid and the reaction is allowed to proceed, under agitation, at a temperature of 0° to 5° C. for a period of 42 hours. The reaction mixture is centrifuged and the dialdehydestarch precipitate is then washed with water to remove all traces of inorganic salts.

Thereafter, a reaction vessel fitted with a condenser, a drying tube and means for mechanical agitation, is charged with a solution of 3.8 parts of dinitrogen tetroxide in 250 parts of dry carbon tetrachloride. This solution is vigorously agitated, whereupon 4.0 parts of the above prepared dialdehydestarch is incrementally added thereto. The reaction is allowed to proceed at room temperature for a period of 22 hours. The mixture is then recharged with 3.8 parts of dinitrogen tetroxide and the reaction is allowed to proceed for an additional 48 hours. The excess dinitrogen tetroxide is removed by bubbling nitrogen gas through the system until the red nitrous oxide fumes have substantially disappeared. The white solid product is then filtered, washed with water and dried.

EXAMPLE IV

The following is another representative toothpaste of the present invention.

| Component | Wt % |
|---|---|
| Sorbitol (70% Aqueous Solution) | 50.75 |
| Distilled Water | 16.50 |
| Sodium Saccharin | 0.30 |
| Dye Solution | 0.35 |
| Precipitated Silica | 20.00 |
| Sodium Fluoride | 0.25 |
| Flavor | 1.30 |
| Sodium Alkyl Sulfate (27.9% Aqueous Solution) | 5.00 |
| Carbopol 940s | 0.20 |
| Xanthan Gum | 0.60 |
| Carboxy Starch Polymer of Example III | 4.15 |
| | 100.00 |

In addition to the levels and combinations of ingredients shown in these examples, others can be used which are consistent with the invention disclosed.

EXAMPLE V

This example illustrates the preparation of a typical carboxy starch polymer of this invention.

A reaction vessel is charged with 49.1 g of commercial non-defatted cornstarch and 300 mls of water at 25° C. to form a suspension. 71.3 g of unbuffered sodium metaperiodite in 910 ml. of water are added to this suspension to form a reaction mixture. The reaction is allowed to proceed, under agitation, at room temperature for a period of 22 hours. The reaction mixture is filtered and the dialdehyde starch precipitate is then washed with water to remove any traces of inorganic salts.

Thereafter, 45 g of the dialdehyde starch precipitate is charged into an open beaker. 203 g of 1 M $NaClO_2$ and 64 ml. of glacial acetic acid are then added to the open beaker to form a slurried reaction mixture. The oxidation reaction of the dialdehyde starch is allowed to proceed, under agitation, at room temperature for a period of 22 hours. As the reaction progresses, the reaction mixture changes from a light yellow to an orange color with the evolution of a considerable quantity of chlorine dioxide gas. At the conclusion of the reaction nitrogen is bubbled through the reaction mixture to remove all but traces of chlorine dioxide, and the solution is adjusted to a pH ranging from 8 to 9 with 50% NaOH solution.

The oxidized product is precipitated by pouring the reaction mixture, with rapid stirring, into 2 volumes of absolute ethanol, and then filtered. The filtered starches are then reprecipitated in this manner to afford 9.4 g of carboxy starch having a degree of carboxylation of 1.9.

EXAMPLE VI

This example shows a mouth rinse composition containing a carboxy starch polymer of the present invention The mouth rinse is prepared as follows:

| Component | Wt % |
|---|---|
| Carboxy Starch Polymer of Example V | 4.00 |
| Distilled $H_2O$ | 69.19 |
| Ethanol | 16.25 |
| Glycerin | 10.00 |
| Nonionic Surfactant | 0.12 |
| Benzoic Acid | 0.05 |
| Sodium Saccharin | 0.05 |
| Flavor | 0.15 |
| Color | 0.04 |
| NaOH (10% Sol.) | 0.15 |
| | 100.00 |

The mouth rinse is prepared by adding each of the ingredients to the distilled water and stirring.

What is claimed is:

1. An oral composition comprising: (a) a safe and effective amount of a plaque-inhibiting starch polymer comprising the formula

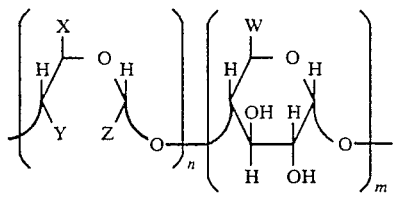

wherein W and X are independently selected from $CH_2OH$, CHO and $CO_2H$, or the neutralized carboxylic acid salts thereof, Y and Z are independently selected from CHO and $CO_2H$, or the neutralized carboxylic acid salts thereof, n is in the range of from about 5 to about 2500, m is in the range of from 0 to about 2500, provided that the sum of n and m ranges from about 5 to about 2500, and the degree of carboxylation of said polymer ranges from about 1 to about 3; and (b) a pharmaceutically acceptable carrier.

2. An oral composition according to claim wherein the degree of carboxylation of the active agent in (a) ranges from about 1.5 to about 3.

3. An oral composition according to claim 2 wherein the degree of carboxylation of the active agent in (a) ranges from about 1.7 to about 3.

4. An oral composition according to claim 2 wherein the mass average molecular weight of the active agent in (a) ranges from about 1,000 to about 500,000.

5. An oral composition according to claim 4 wherein the mass average molecular weight of the active agent in (a) ranges from about 1,000 to about 300,000.

6. An oral composition according to claim 5 which comprises from about 0.1% to about 10% by weight of the active agent in (a).

7. An oral composition according to claim 5 which comprises from about 1% to about 8% by weight of the active agent in (a).

8. An oral composition according to claim 7 which comprises from about 3% to about 5% by weight of the active agent in (a).

9. An oral composition according to claim 8 wherein X is selected from $CH_2OH$ and $CO_2H$ and W is $CH_2OH$, or the neutralized carboxylic acid salts thereof.

10. An oral composition according to claim 9 wherein X is $CH_2OH$, Y is $CO_2H$ and Z is $CO_2H$, or the neutralized carboxylic acid salts thereof.

11. An oral composition according to claim 9 wherein the mass average molecular weight of the active agent in (a) ranges from about 50,000 to about 250,000.

12. An oral composition according to claim 9 wherein X is $CO_2H$, Y is $CO_2H$, Z is $CO_2H$, or the neutralized carboxylic acid salts thereof, n is in the range of from about 5 to about 250, and m is in the range of from 0 to about 250, provided that the sum of n and m is in the range of from about 5 to about 250.

13. An oral composition according to claim 12 wherein the mass average molecular weight of the active agent in (a) ranges from about 1,000 to about 20,000.

14. An oral composition according to claim 6 which additionally contains a safe and effective amount of a fluoride ion source.

15. An oral composition according to claim 14 wherein the fluoride ion source is sodium fluoride present at a concentration ranging from about 0.005% to about 2.0% by weight.

16. An oral composition according to claim 15 wherein the pharmaceutically acceptable carrier is a toothpaste.

17. An oral composition according to claim 16 which also contains a silica dental abrasive.

18. An oral composition according to claim 15 wherein the pharmaceutically acceptable carrier is a mouthwash.

19. An oral composition according to claim 15 wherein the pharmaceutically acceptable carrier is a topical dental gel.

20. An oral composition according to claim 15 wherein the pharmaceutically acceptable carrier is a lozenge.

21. An oral composition according to claim 15 wherein the pharmaceutically acceptable carrier is a chewing gum.

22. A method of inhibiting plaque formation in the oral cavity comprising applying a safe and effective amount of the composition according to claim 1 to the oral cavity.

23. A method according to claim 22 wherein the composition is in the form of a toothpaste.

24. A method according to claim 22 wherein the composition is in the form of a mouthwash.

25. A method according to claim 22 wherein the composition is in the form of a dental gel.

26. A method according to claim 22 wherein the composition additionally contains sodium fluoride at a concentration ranging from about 0.005% to about 2.0% by weight.

* * * * *